(12) United States Patent
Doshi et al.

(10) Patent No.: US 11,371,976 B2
(45) Date of Patent: Jun. 28, 2022

(54) SYSTEMS AND METHODS FOR AN SOC BASED ELECTRONIC SYSTEM FOR DETECTING MULTIPLE LOW CONCENTRATION GAS LEVELS

(71) Applicant: AerNos, Inc., San Diego, CA (US)

(72) Inventors: Sundip R. Doshi, San Diego, CA (US); Moazzem Hossain, San Jose, CA (US); Herve Lambert, Coronado, CA (US); Albert Chen, Poway, CA (US)

(73) Assignee: AERNOS, INC., San Diego, CA (US)

( * ) Notice: Subject to any disclaimer, the term of this patent is extended or adjusted under 35 U.S.C. 154(b) by 0 days.

(21) Appl. No.: 16/858,313

(22) Filed: Apr. 24, 2020

(65) Prior Publication Data

US 2020/0256840 A1 Aug. 13, 2020

Related U.S. Application Data

(63) Continuation-in-part of application No. 16/547,499, filed on Aug. 21, 2019.
(Continued)

(51) Int. Cl.
*G01N 33/00* (2006.01)
*G01N 27/22* (2006.01)
*G01N 27/12* (2006.01)

(52) U.S. Cl.
CPC ....... *G01N 33/0034* (2013.01); *G01N 27/121* (2013.01); *G01N 27/122* (2013.01);
(Continued)

(58) Field of Classification Search
CPC ............. G01N 33/0034; G01N 27/121; G01N 27/122; G01N 27/223; G01N 27/227;
(Continued)

(56) References Cited

U.S. PATENT DOCUMENTS 3,610,953 A * 10/1971 Gordon .............. H03K 17/6871
327/430
4,542,640 A 9/1985 Clifford
(Continued)

FOREIGN PATENT DOCUMENTS

| GB | 2533294 A | 6/2016 |
| JP | 2012511714 A | 5/2012 |
| WO | 2016145300 A1 | 9/2016 |

OTHER PUBLICATIONS

Sofian M. Kanan, et al. Semiconducting Metal Oxide Based Sensors for Selective Gas Pollutant Detection, Oct. 2009, Sensors 9(10), 8158-8196 (Year: 2009).
(Continued)

*Primary Examiner* — Tung X Nguyen
*Assistant Examiner* — Feba Pothen
(74) *Attorney, Agent, or Firm* — Procopio, Cory, Hargreaves & Savitch LLP

(57) ABSTRACT

A sensor system in a package, comprising: a package, the package including: a sensor chip comprising sensor array comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when the interacting with gaseous chemical compounds; and a mixed signal System on a Chip (SoC), comprising an analog signal conditioning and Analog-to-Digital conversion circuit configured to convert the analog signal into a digital signal, and a low-power processor circuit configured to processes the digital signal using a pattern
(Continued)

recognition system implementing gas detection and measurement algorithms.

23 Claims, 15 Drawing Sheets
(4 of 15 Drawing Sheet(s) Filed in Color)

Related U.S. Application Data

(60) Provisional application No. 62/799,466, filed on Jan. 31, 2019, provisional application No. 62/721,306, filed on Aug. 22, 2018, provisional application No. 62/721,311, filed on Aug. 22, 2018, provisional application No. 62/721,293, filed on Aug. 22, 2018, provisional application No. 62/721,289, filed on Aug. 22, 2018, provisional application No. 62/721,309, filed on Aug. 22, 2018, provisional application No. 62/721,302, filed on Aug. 22, 2018, provisional application No. 62/721,296, filed on Aug. 22, 2018.

(52) U.S. Cl.
CPC ......... *G01N 27/128* (2013.01); *G01N 27/223* (2013.01); *G01N 27/227* (2013.01); *G01N 27/228* (2013.01); *G01N 2033/0068* (2013.01)

(58) Field of Classification Search
CPC ............... G01N 27/228; G01N 27/128; G01N 2033/0068; G01N 2027/222; G01N 27/127
See application file for complete search history.

(56) References Cited

U.S. PATENT DOCUMENTS

| | | | |
|---|---|---|---|
| 4,736,433 A | 4/1988 | Dolby | |
| 9,612,993 B2 * | 4/2017 | Field | G06F 1/266 |
| 9,696,311 B2 | 7/2017 | Haick et al. | |
| 2008/0093226 A1 | 4/2008 | Star et al. | |
| 2009/0075414 A1 | 3/2009 | Lee et al. | |
| 2010/0116682 A1 | 5/2010 | Neuzil et al. | |
| 2010/0147684 A1 | 6/2010 | Park et al. | |
| 2010/0323925 A1 | 12/2010 | Gabriel et al. | |
| 2012/0133422 A1 | 5/2012 | Pereira da Silva, Jr. et al. | |
| 2012/0265474 A1 * | 10/2012 | Rearick | G01N 27/4165 702/104 |
| 2013/0062211 A1 | 3/2013 | Deshusses et al. | |
| 2013/0075794 A1 | 3/2013 | Bradley et al. | |
| 2014/0262776 A1 | 9/2014 | Martin et al. | |
| 2015/0268207 A1 | 9/2015 | Motayed | |
| 2015/0323510 A1 | 11/2015 | Huynh et al. | |
| 2015/0378954 A1 | 12/2015 | Field et al. | |
| 2016/0238553 A1 | 8/2016 | Shachar | |
| 2016/0334359 A1 | 11/2016 | Kim et al. | |
| 2017/0350936 A1 | 12/2017 | McMeen et al. | |
| 2018/0003660 A1 | 1/2018 | Tayebi et al. | |
| 2018/0074003 A1 * | 3/2018 | Novac | G01N 27/121 |
| 2018/0136158 A1 | 5/2018 | García González et al. | |
| 2018/0284737 A1 | 10/2018 | Cella et al. | |
| 2019/0025237 A1 | 1/2019 | Kelly et al. | |
| 2019/0250135 A1 | 8/2019 | Andersson et al. | |
| 2020/0064321 A1 | 2/2020 | Chen et al. | |
| 2020/0256840 A1 | 8/2020 | Doshi et al. | |

OTHER PUBLICATIONS

Syed Mubeen et al., "Hybrid tin oxide-SWNT nanostructures based gas sensor", Mar. 2013, Electrochimica Acta, 92, p. 484-490 (Year: 2013).

Ajeet Kaushik et al., "Organic-Inorganic Hybrid Nanocomposite-Based Gas Sensors for Enfironmental Monitoring", 2015, Chem Ref. 115,11,4571-4606 (Year: 2015).

International Preliminary Reporton Patentability for PCTUS2019/04//91 dated Dec. 5, 2019, 11 pages.

Brust, Mathias et al., "Synthesis of Thiol-derivatised Gold Nanoparticles in a Two-Phase Liquid-Liquid System", 1994, J Chem Soc Chern Commun, 7:801-802 (Year: 1994).

Su, Single Walled Carbon Nanotube Based Hybrid Nanostructure Gas Sensor Array for Air Quality Index, 2014, pp. 6-36 (Year: 2014).

Su et al., "Metal nanoparticles and DNA co-functionalized single-walled carbon nanotube gas sensors", 2013, Nanotechnology, 24 (Year: 2013).

Zhang et al., "A Rapid Room-Temperature NO2 Sensor Based on Tellurium-SWNT Hybrid Nanostructures", 2012, J Phys. Chem. C, 116, 20067-20074 (Year: 2012).

Jung et al., "Enhanced humidity-sensing response of metal oxide coated carbon nanotube,", 2015, Sensors and Actuators A, 223. 11-17 (Year: 2015).

International Search Report and Written Opinion for PCT/US21/28623 dated Jul. 27, 2021, 13 pages.

Murali, Pramod, et al. "A CMOS gas sensor array platform with Fourier transform based impedance spectroscopy." IEEE Transactions on Circuits and Systems I: Regular Papers 59.11 (2012): 2507-2517 (Year: 2012).

Virji, Shabnam et al., "Polyaniline nanofibre gas sensors: examination of response mechanisms." Nano letters 4.3 (2004): 491-496. (Year: 2004).

Li, Haitao, et al. "Low power multimode electrochemical gas sensor array system for wearable health and safety monitoring." IEEE Sensors Journal 14.10 (201): 3391-3399. (Year: 2014).

Chen, Yin-sheng, et al., "Fault detection, isolation, and diagnosis of status self-validating gas sensor arrays." Review of Scientific Instruments 87.4 (2016): 045001. (Year: 2016).

\* cited by examiner

SYSTEMS AND METHODS FOR AN SOC BASED ELECTRONIC SYSTEM FOR DETECTING MULTIPLE LOW CONCENTRATION GAS LEVELS

CROSS-REFERENCE TO RELATED APPLICATIONS

This application is a continuation-in-part of U.S. patent application Ser. No. 16/547,499, filed Aug. 21, 2019, which claims priority to U.S. Provisional Patent Application No. 62/721,289, filed Aug. 22, 2018, U.S. Provisional Patent Application No. 62/721,293, filed Aug. 22, 2018, U.S. Provisional Patent Application No. 62/721,296, filed Aug. 22, 2018, U.S. Provisional Application No. 62/721,302, filed Aug. 22, 2018, U.S. Provisional Patent Application No. 62/721,306, filed Aug. 22, 2018, U.S. Provisional Patent Application No. 62/721,309, filed Aug. 22, 2018, U.S. Provisional Application No. 62/721,311, filed Aug. 22, 2018, U.S. Provisional Patent Application No. 62/799,466, filed Jan. 31, 2019, the contents of which are incorporated herein by reference.

BACKGROUND

1. Technical Field

The embodiments herein relate to the detection and measurement of the absolute concentration of multiple gases at the same time and, in particular, to the sensing of gases by a hybrid nanostructure array in conjunction with electronics and algorithms to selectively identify and measure the concentration of individual gases, in conjunction with highly integrated implementation techniques for the electronics and state-of-the-art multi-chip packaging technology to achieve smallest achievable product form factor and power consumption, and in conjunction with a Cloud database to enable the capture, normalization, and transformation of very large amount of granular sensor information into actionable insight.

2. Related Art

Commercially available gas sensors can be cumbersome to use, expensive and limited in performance (e.g. accuracy, selectivity, lowest detection limit, etc.). In addition, other major drawbacks may include inability to detect different types of gases at the same time, inability to measure absolute concentration of individual gases, the requirement for frequent re-calibration, a size incompatible with integration into small form factor systems such as wearable devices, the reliance on power-hungry techniques such as heating or on technologies not well suited to manufacturing in very high volume.

The ability to accurately detect multiple gases at the same time, often at parts-per-billion (PPB) sensitivity is becoming crucial to a growing number of industries as well as to the world-wide expansion of air quality monitoring initiatives aiming to address household and urban air pollution challenges.

The continuous collection of highly granular gas information by a multitude of connected devices (IoT—Internet of Things) is critical to go beyond monitoring to generate actionable insight from large amount of collected data (Big Data Analytics, Artificial Intelligence).

IoT devices cover a wide spectrum of applications and often require highly integrated solutions to support aggressive power/performance targets, challenging form factors (e.g. small, battery-powered wearable devices), and product costs suitable for intended target markets and a very high-volume deployment.

SUMMARY

Systems and methods to combine a nanohybrid gas sensor chip, utilizing highly sensitive nano nucleated structures, together with a mixed signals System-On-a-Chip (SoC) in a single, small, and very thin package to deliver the key fundamental attributes required for the broad deployment of sensors capable of low detection limits (PPB) in support of highly granular collection of gas information in ambient air are described herein.

According to one aspect, a sensor system in a package, comprising: a package, the package including: a sensor chip comprising sensor array comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when interacting with gaseous chemical compounds; and a mixed signal System on a Chip (SoC), comprising an analog signal conditioning and Analog-to-Digital conversion circuit configured to convert the analog signal into a digital signal, and a low-power processor circuit configured to processes the digital signal using a pattern recognition system implementing gas detection and measurement algorithms.

BRIEF DESCRIPTION OF DRAWINGS

The patent or application file contains at least one drawing executed in color. Copies of this patent or patent application publication with color drawing(s) will be provided by the Office upon request and payment of the necessary fee.

These and other features, aspects, and embodiments are described below in the section entitled "Detailed Description."

DETAILED DESCRIPTION

Figure 1:
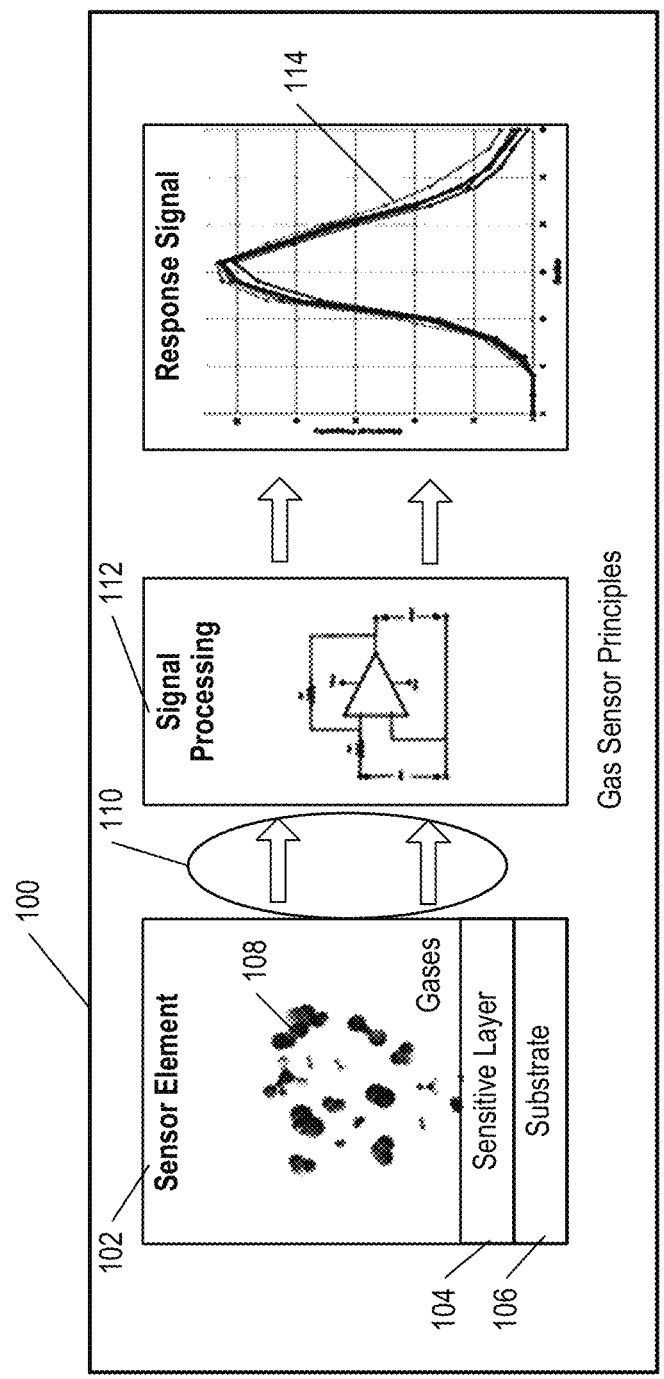
FIG. 1 illustrates the basic principles to construct a gas sensor.

Embodiments for a hybrid nanostructure gas sensing system are described herein. The disclosure and the various features and advantageous details thereof are explained more fully with reference to the non-limiting embodiments and examples that are described and/or illustrated in the accompanying drawings and detailed in the following. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The architecture embodied in the hybrid nanostructure gas sensing system described herein achieves the basic requirement of selectively identifying the presence of a gas analyte in diverse mixtures of ambient air but it is also designed to identify multiple gases at the same time, to be compatible in terms of size and power with very small form factors (including for mobile and wearable applications), to be easy to Integrate in IoT applications and to be self-calibrating, thus unshackling the application and/or the service provider from the burden and expense of regular re-calibration.

FIG. 1 describes the basic ingredients for a successful gas sensor 100. As can be seen, such a sensor includes a sensing element 102 that is created by depositing a sensitive layer 104 over a substrate 106. The sensing element 102 can then interact with gaseous chemical compounds 108 altering one or more electrical properties of the sensing element 102. The change in electrical properties can be detected by feeding the sensor raw signals 110 through specially designed signal processing electronics 112. The resulting response signals 114 can be measured and quantified directly or through the application of pattern recognition techniques.

The embodiments described herein comprise six basic elements. The first is the basic sensor element or sensing channel, which combines a structural component, built on a substrate suitable for reliable high-volume manufacturing (some examples described below), with a deposited electrolyte containing hybrid nano structures in suspension. The formulation of the electrolyte is specific to a particular gas or family of gases. A silicon substrate 106 and the structural component can be built using a MEMS manufacturing process. The structural component is essentially an unfinished electrical circuit between two electrodes. The deposition of the electrolyte completes the electrical circuit and, when biased and exposed to gas analytes, changes to one or more of the electrical characteristics of the circuit are used to detect and measure gases.

The second element is the arrangement of multiple sensing channels into an array structure specifically designed and optimized to interface with data acquisition electronics 112. The array structure, combined with the use of pattern recognition algorithms, makes it possible to detect multiple gases at the same time with a single sensor by customizing one or more of the individual sensing channels in the array for a specific gas or family of gases while using other sensing channels to facilitate such critical functions as selectivity.

Figure 2:
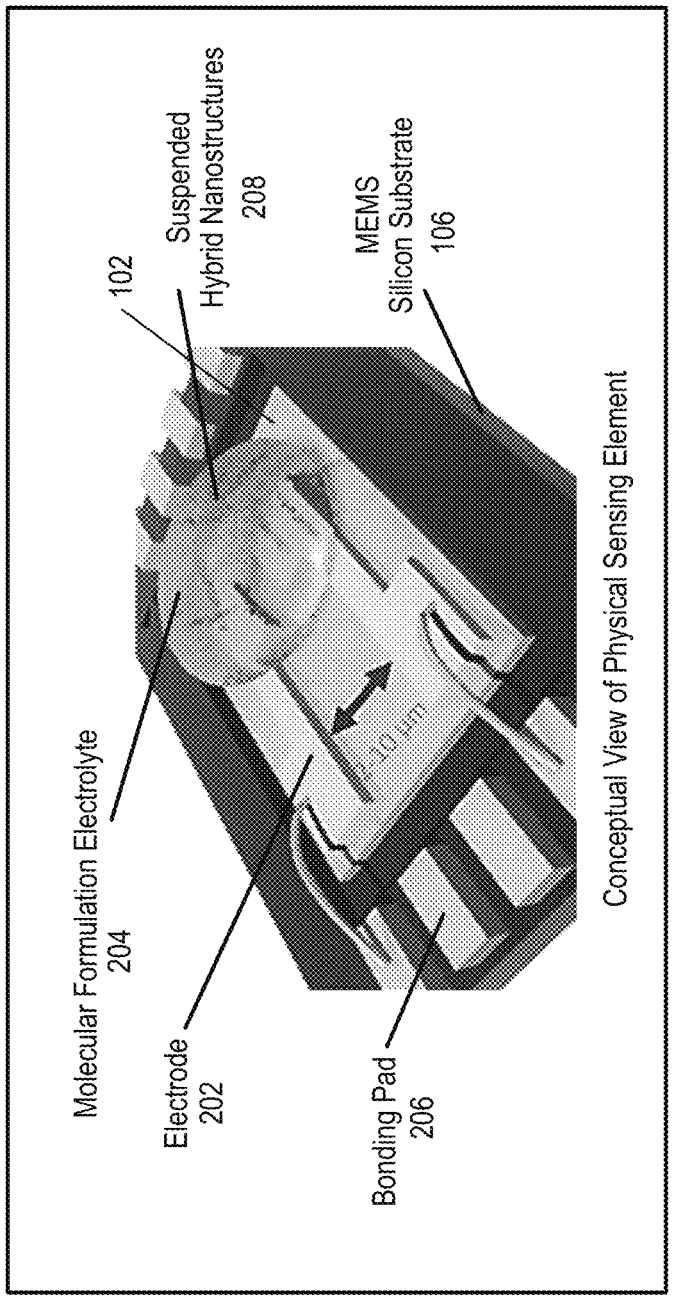
FIG. 2 is a prospective view of a physical implementation of a hybrid nanostructure gas sensing element in accordance with one embodiment.

FIG. 2 is a conceptual view of a hybrid nanostructure physical sensing element 102 in accordance with one example embodiment. Different materials can be used for the substrate 106 on which the rest of the sensing element 102 is constructed. But from the perspective of very high volume manufacturing, silicon technology can be preferred and specifically MEMS technology, which provides the necessary foundation for a customer-defined set of manufacturing steps with the flexibility to modulate the complexity of the process based on the sophistication of the sensor chip being built, e.g., to support further innovation or to address special product needs. Silicon technology also provides access to time-proven test methods and multiple sources of Automated Test Equipment that can be customized to fit the needs of gas sensing technology.

The sensing element 102 is made of an incomplete or "open" electrical circuit between two electrodes 202, which is then completed or "closed" by depositing, a molecular formulation electrolyte 204 with hybrid nanostructures 208 in suspension. The process is compatible with several commonly used deposition techniques but does require specially customized equipment and proprietary techniques to achieve the desired quality and reproducibility in a high-volume manufacturing environment. In certain embodiments, the sensing element 102 can be specially patterned to support efficient deposition of nanomaterial in pico-litter amounts and to facilitate incorporation of multiple elements into an array to enables the design of multi-gas sensors.

Electrodes 202 can then be bonded to bonding pads 206 in order to communicate signals 110 to the rest of the system.

One or more molecular formulations may be necessary to completely and selectively identify a particular gas. Combining multiple sensing elements 102, each capable of being "programmed" with a unique formulation, into a sensor array provides the flexibility necessary to detect and measure multiple gases at the same time. It also enables rich functional options such as for instance measuring humidity, an important factor to be accounted for in any gas sensor design, directly on the sensor chip (after all water vapor is just another gas). Another example is the combination for the same gas or family of gases of a formulation capable of very fast reaction to the presence of the gas while another formulation, slower acting, may be used for accurate concentration measurement; this would be important in applications where a very fast warning to the presence of a dangerous substance is required but actual accurate concentration measurement may not be needed at the same time (e.g. first responders in an industrial emergency situation).

Figure 3:
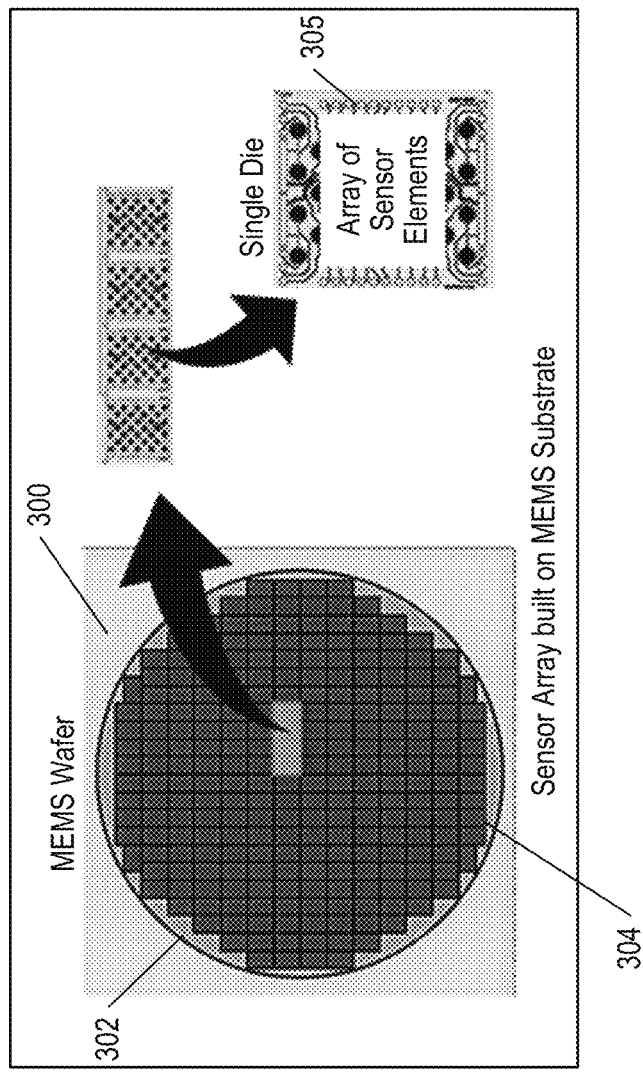
FIG. 3 is a diagram illustrating an embodiment of a gas sensor array that can be included in the hybrid nanostructure gas sensing element of FIG. 2.

FIG. 3 illustrates the preferred embodiment of a multichannel, gas sensor array 305 where a silicon substrate 302 is used with a MEMS manufacturing process to build the structure of the sensing channels on which the molecular formulations 204 can be deposited. For illustration purposes the size of the individual sensor die 304 is shown as being much larger than achievable in practice; a single 8" wafer 300 will typically yield several thousand multi-gas capable sensor chips. An array 305 of sensing elements 102 is implemented on a single die 304 and each wafer 300 yields several thousand dies, or chips 304. Each sensing element 102 can then be functionalized by depositing a specific molecular formulation 204 thereon.

Thus, after MEMS manufacturing, additional steps are required to complete the fabrication of each sensing element 102. First, molecular formulations 204 are deposited and cured using specialized equipment. This happens at wafer level and the equipment is designed in a modular fashion to allow for the scaling of the output of a manufacturing facility by duplicating modules and fabrication processes in a copy-exactly fashion. After completion of the manufacturing steps, the wafers 300 must be singulated using a clean dicing technology in order to prevent damage to the sensing elements 102. An example of such technology is Stealth dicing.

The third element is the electronic transducer that detects changes in the electrical characteristics of the sensor array 305, provides signal conditioning and converts the analog signal from the sensor elements 102 into a digital form usable by the data acquisition system, described in more detail below. As described below, the transducer can be a low voltage analog circuit that provides biasing to the array of sensing channels and two functional modes: parking and measurement. Sensing channels are in parking mode either when not in measurement mode or when not used/enabled at all for a given application. The circuitry can be designed to maintain the sensing channels in a linear region of operation, to optimize power consumption, to enable any combination of channels in either parking or measurement modes and to provide a seamless transition between modes.

Figure 5:
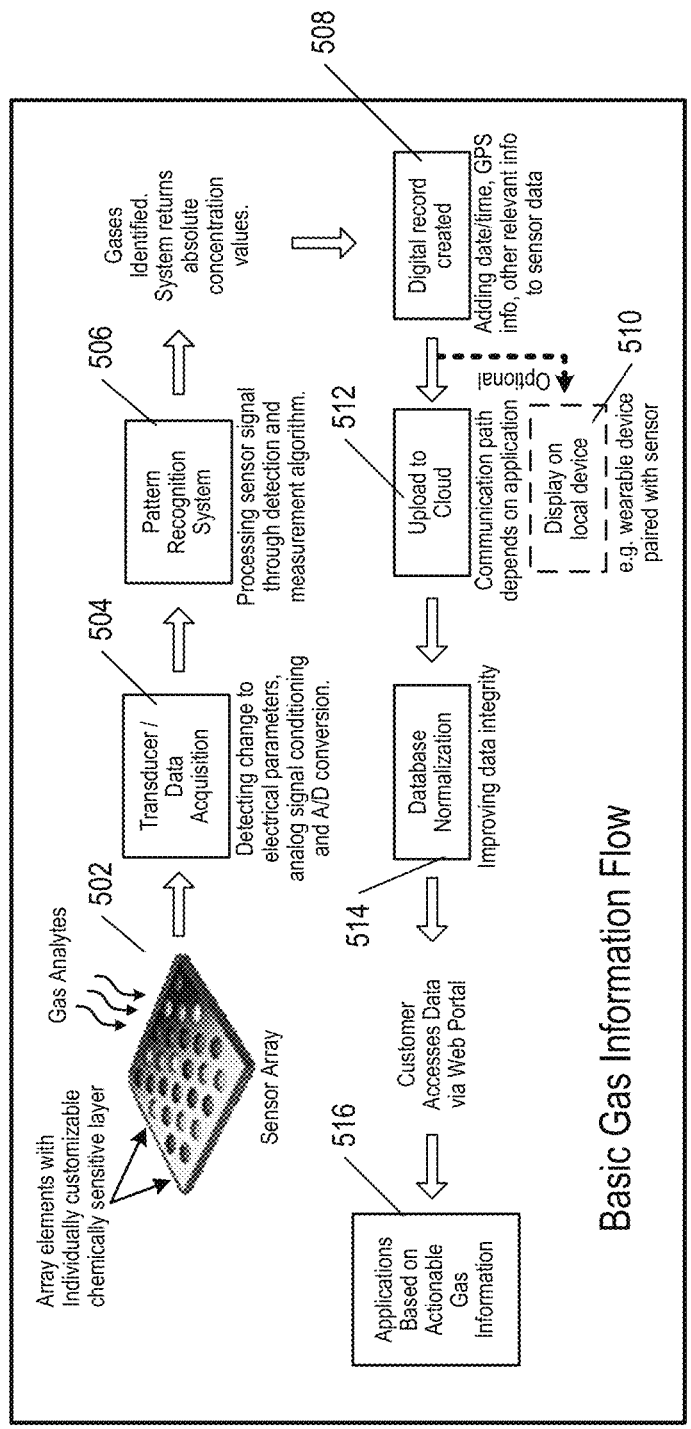
FIG. 5 is a chart showing the flow of gas information through the hybrid nanostructure gas sensor system of FIG. 4.

FIG. 5 shows the basic flow of information through a complete nano gas sensor system, such as system 400 described in more detail below. When the sensor array 305 is exposed to the mixture of gas analytes 108 in its environment, in step 502, the sensitive layers 104 of the materials deposited on the sensor elements 102, or sensing channels react, according to their formulation 202, to the presence of specific component gases in the mixture. The reaction causes a change in the electrical characteristics of the sensing channels 102, which is captured by the transducer in the electronics sub-system, in step 504, and then analyzed by the pattern recognition system programmed in the sub-system MCU, in step 506. The output is an absolute value of the concentration of the gases being detected. This is then combined, in step 508, with other desirable meta-data such as time or geo-location into a digital record. This digital record (or a portion of it) can optionally be displayed locally in step 510 (for example, in the case of a wearable application where the sensor is paired to a phone, the data can be further manipulated and displayed by a specially written mobile application running on the phone). More importantly the data is uploaded, via a mechanism that is dependent on the application, to a Cloud data platform in step 512, where the data can be normalized in step 514 and accessed via various application in step 516.

The fourth element is a MCU-based data acquisition and measurement engine, which also provides additional functions such as overall sensor system management and communication, as necessary with encryption, to and from a larger system into which the sensor is embedded.

The third and fourth elements are designed to work together and to form a complete electronic sub-system specifically tuned to work with the array of sensing channels 305 implemented as a separate component. The transducer 404 is firmware configurable to provide optimal A/D conversion for a pattern recognition system running on the MCU 406 and implementing the gas detection and measurement algorithm(s).

The electronic sub-system 402 is suitable for implementation in a variety of technologies depending on target use model and technical/cost trade-offs. PCB implementations will enable quick turn-around and the declination of a family of related products (for instance with different communication interfaces) to support multiple form factors and applications with the same core electronics. When size and power/performance trade-offs are critical, the electronic sub-system 402 is implemented as a System On a Chip (SoC), which can then be integrated together with a MEMS chip carrying the array of sensing channels 305 into a System In a Package (SIP).

Figure 4:
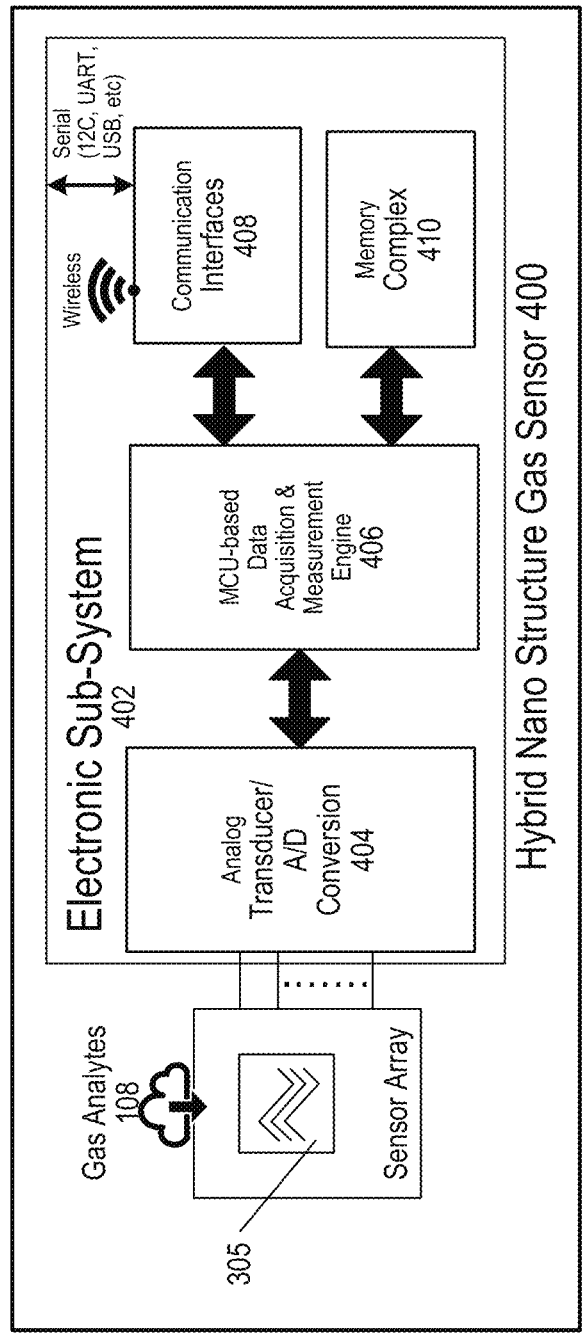
FIG. 4 is a block diagram of the hybrid nanostructure gas sensor system that incorporates the hybrid nanostructure gas sensing element of FIG. 2 in accordance with one embodiment.

The sensor die 304 must then be assembled with the sensor's electronic sub-system to complete the hybrid nanostructure gas sensor 400 for which a functional block diagram is shown in FIG. 4.

The electronic sub-system can be implemented as a PCB or as a SoC. If the PCB route is followed the sensor die 304 can be either wire-bonded to the electronic sub-system 402 board after completion of the PCB Assembly (PCBA) step or, if the sensor die 304 has itself been individually assembled in a SMT package, it can be soldered on the board as part of PCBA. If the SoC route is followed, the sensor die together with the SoC die of the electronic sub-system 402 can be stacked and assembled together into a single package (System In a Package) or each can possibly be assembled into individual packages.

Either assembled into its own package or assembled into a SIP, the sensor chip 304 must be exposed to ambient air. Therefore, the package lid must include a hole of sufficient size over the sensor.

Testing happens at various points of the sensor manufacturing process.

After sensor functionalization (deposition of the molecular formulations 204), certain handling precautions must be followed for the rest of the product manufacturing flow to prevent accidental damage to the sensor chip 304 (e.g. a pick and place tool must not make contact with the surface of the sensing elements).

The fifth element is the gas detection and measurement algorithm. The algorithm implements a method for predicting target gas concentration by reading the hybrid nanostructure sensor array's multivariate output and processing it inside the algorithm. The algorithm analyzes sensor signals in real time and outputs estimated values for concentrations of target gases. The algorithm development is based on models that are specific to the materials deposited on the sensing channels of the sensor array. These models are trained based on the collection of an abundant volume of data in the laboratory (multiple concentrations of target gases, combinations of gases, various values of temperature, relative humidity and other environmental parameters). Sophisticated supervised modeling techniques are used to attain the best possible agreement between true and predicted values of target gas concentrations. Prior to deployment, extensive lab and field testing is carried out to optimize model performance and finalize sensor validation.

The first five elements together constitute the hybrid nanostructure gas sensor 400 and provide all the functionality necessary to detect multiple gases 108 in ambient air at the same time and to report their absolute concentrations. The sensing capability of the hybrid nanostructure sensor array 305 is always "on" and the gas detection and measurement algorithm makes it possible for the sensor 400 to require no special calibration step before use and to remain self-calibrating through its operational life.

The sixth element is the Cloud Data Platform that enables a virtually unlimited number of sensors 400 deployed as part of a virtually unlimited number of applications to be hosted in a global database where big data techniques can be used to analyze, query and visualize the information to infer actionable insight. The use of a Cloud-based environment provides all the necessary flexibility to customize how the data can be partitioned, organized, protected and accessed based on the rights of individual tenants.

The Cloud data platform provides another layer of sophistication to the system by allowing Cloud applications to operate on the data set. For instance, sensors 400 that are located in the same vicinity would typically report consistent gas values thus allowing errant results to be identified and a possible malfunction of one node of a network of sensors investigated.

The continuous collection of highly granular gas information by a multitude of connected devices (IoT—Internet Of Things) is critical to go beyond monitoring to generate actionable insight from large amount of collected data (Big Data Analytics, Artificial Intelligence).

A few application examples are highlighted below.

Example 1

We take 20,000 breaths every day and the air we breathe impacts our health—the science is already clear on this—but we rarely know what is in the air we breathe. To take meaningful action, consumers, scientists, public officials and business owners need the ability to measure air pollution at a personal, local and granular level which has, before this invention, been impossible due to the limitations of commercially available gas sensors mentioned above.

Mounting evidence suggests that prenatal and early life exposure to common environmental toxins, such as air pollution from fossil fuels, can cause lasting damage to the developing human brain. These effects are especially pronounced in highly vulnerable fetuses, babies, and toddlers as most of the brain's structural and functional architecture is established during these early developmental periods. These disruptions to healthy brain development can cause various cognitive, emotional, and behavioral problems in later infancy and childhood.

The sensor technology described herein allows researchers to gather highly detailed, accurate data about pregnant women's exposure to environmental air pollution and the resulting effects on the developing brain. The availability of this technology will represent a profound advance on current methods and efforts in the field that will have far-reaching consequences for improving newborn and child health throughout the world.

More generally, personal air monitoring and local indoor and outdoor monitoring will be a breakthrough for scientific research, healthcare interventions, personal preventive actions, advocacy and more.

The sensor technology described herein can deliver complete processing and gas results to a broad spectrum of smart systems under development for the Smart Cities of tomorrow. The sensor is designed for Plug and Play integration into IoT devices and the small form factor is compatible with a multitude of devices from LED lights to smart meters, to standalone monitoring stations, to non-stationary devices (drones, public vehicles, wearables, phones, etc.).

Example 2

The sensor technology described herein can be used in smart appliances such as connected refrigerators, that will help customers monitor food freshness, detect spoilage and the presence of harmful pesticide residues. The simultaneous, multi-gas, sensing capability of the invention will enable sensors that can recognize the gas patterns associated with the condition of specific foods.

Example 3

A network or grid of the sensors 400 described herein, can be integrated into industrial areas such as petrochemical complexes and oil refineries to allow companies to monitor the sites during regular operation (e.g. for leaks) or in the event of natural or human-made disasters. The sensors can also be installed in drones for data collection in hard to reach or potentially dangerous area. The ability of the technology to be deployed in wearables and in fixed and mobile networks will provide both personal protection and granular data across large area, allow the constant monitoring of a facility for preventive measures to be taken in a timely fashion, save critical time when urgent decision making is required and provide invaluable information to protect workers and emergency personnel.

The same technology can place powerful new tools in the hands of first responders and officials responsible for public safety and homeland security.

Figure 6:
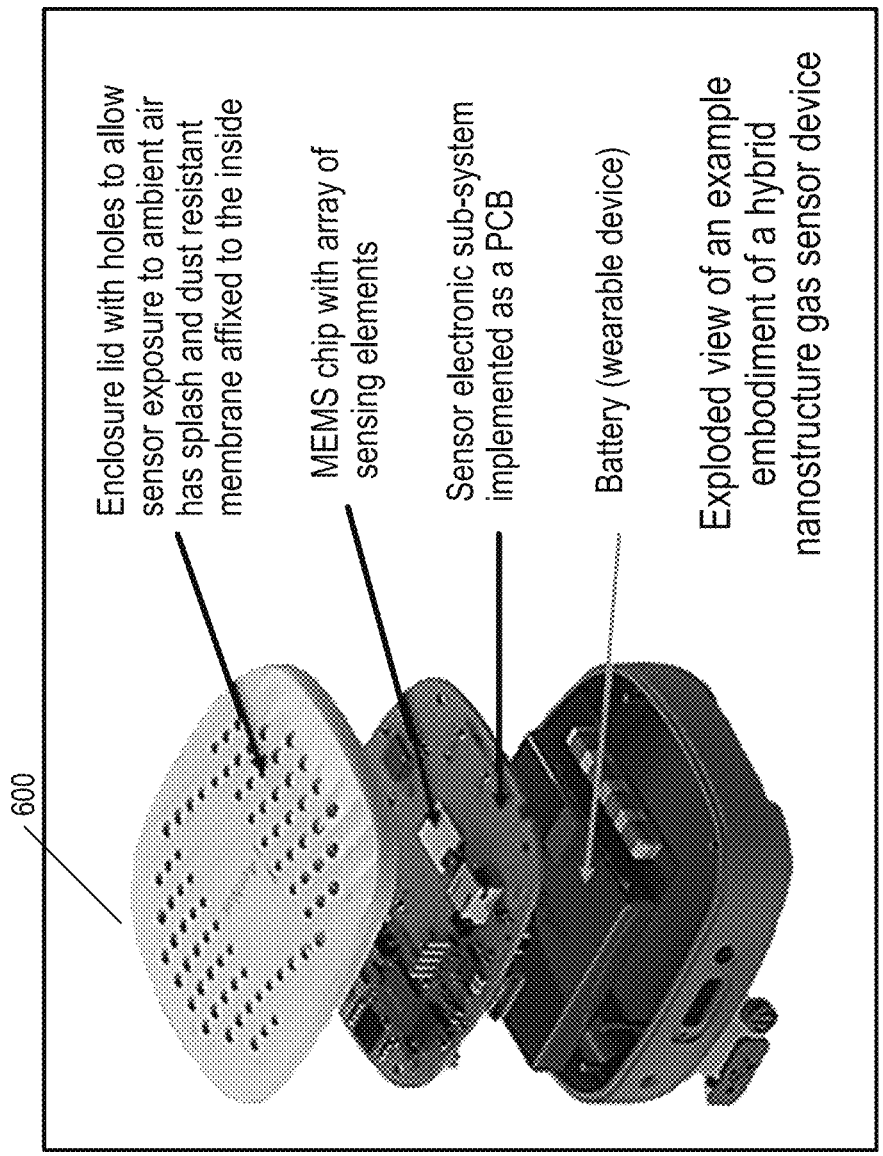
FIG. 6 is an exploded view of an example wearable product built around a PCB embodiment of the hybrid nanostructure gas sensor system of FIG. 4.

FIG. 6 shows an example product 600, in this case a battery-powered wearable device, with the sensor 400 implemented as a small PCB. The sensor technology lends itself to integration into any number of IoT devices. While the sensor does not need the active creation of an airflow to function, the sensitive layers 104 at the surface of the sensor must be exposed to ambient air and at the same time provided a reasonable amount of protection from dust and fluids. This is usually achieved by designing an air interface that ensures that the sensor 400 is behind a perforated shield (e.g. the lid of an enclosure) with a thin membrane (PTFE, 0.5 um mesh) being used to provide splash and dust protection. Outdoor applications may require the design of a more complicated air interface to meet the weather-proofing requirements.

As noted above, the ability to accurately detect multiple gases at the same time, often at parts-per-billion (PPB) sensitivity is becoming crucial to a growing number of industries as well as to the world-wide expansion of air quality monitoring initiatives aiming to address household and urban air pollution challenges. The following outlines in more detail embodiments that combine a nanohybrid gas sensor chip that uses highly sensitive nano-nucleated structures, as described above together with a mixed signals System-On-a-Chip (SoC) in a single, small, and very thin package to deliver the key fundamental attributes required for the broad deployment of sensors capable of low detection limits (PPB) in support of highly granular collection of gas information in ambient air. A hybrid nanostructure gas sensor, as described above, can provide all the functionality necessary to detect multiple gases in ambient air at the same time and to report their absolute concentrations. The sensing capability of the hybrid nanostructure sensor array is always "on", whereas the gas detection and measurement algorithm enable the sensor to require no special calibration step before use and to remain self-calibrating through its operational life.

The mixed signals SoC, described below, combines highly optimized analog electronics with a microcontroller-based digital backend. The analog portion provides bias to the sensor chip and enables "parking" and measurement" functions for each element of the multi-channel gas sensor array, detects changes in electrical properties of the sensing channels, conditions the raw analog signal from the sensor array, and runs the analog signal through an A/D conversion to provide an input signal to the digital back-end. The digital backend includes a powerful, but very low power microcontroller that provides controls to the analog frontend to optimize power delivery, sensor data collection, and gas concentration measurement. The digital backend runs custom pattern recognition algorithms to calculate and report gas concentration values, manages formatting and temporary accumulation/storage of gas information and other related metadata, and controls communications in and out of the system via a selection of serial interfaces.

Both sensor and SoC chips can be stacked and connected into a state-of-the-art custom-designed package to deliver a complete sensor system solution, a System In a Package (SIP) (described in more detail below), suitable for integration into the most aggressive IoT form factors.

Figure 8:
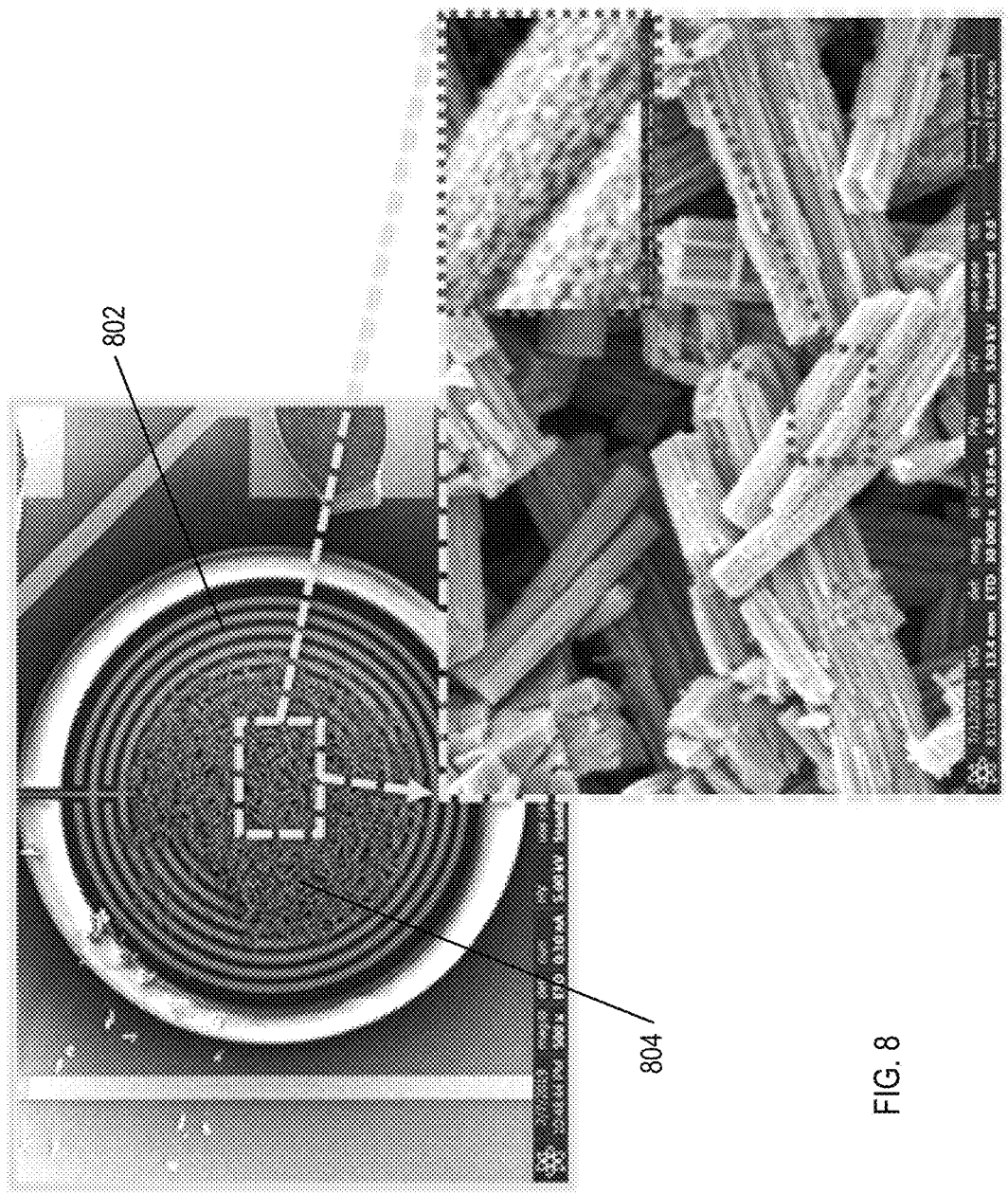
FIG. 8 shows SEM micrographs of highly sensitive AerN2S materials deposited and annealed onto an electrode.

FIG. 8 shows SEM micrographs at various magnifications of highly sensitive nanomaterials 804 deposited and annealed onto an electrode 802. The high surface area nanomaterial is functionalized with atomically dispersed metal catalysts for sensing airborne environmental pollutants. The deposited nanomaterials 804 bridges the gap between the interdigitated fingers of the electrode 402 to connect the circuit within a certain resistance range while also serving as a highly sensitive sensing surface.

Figure 9:
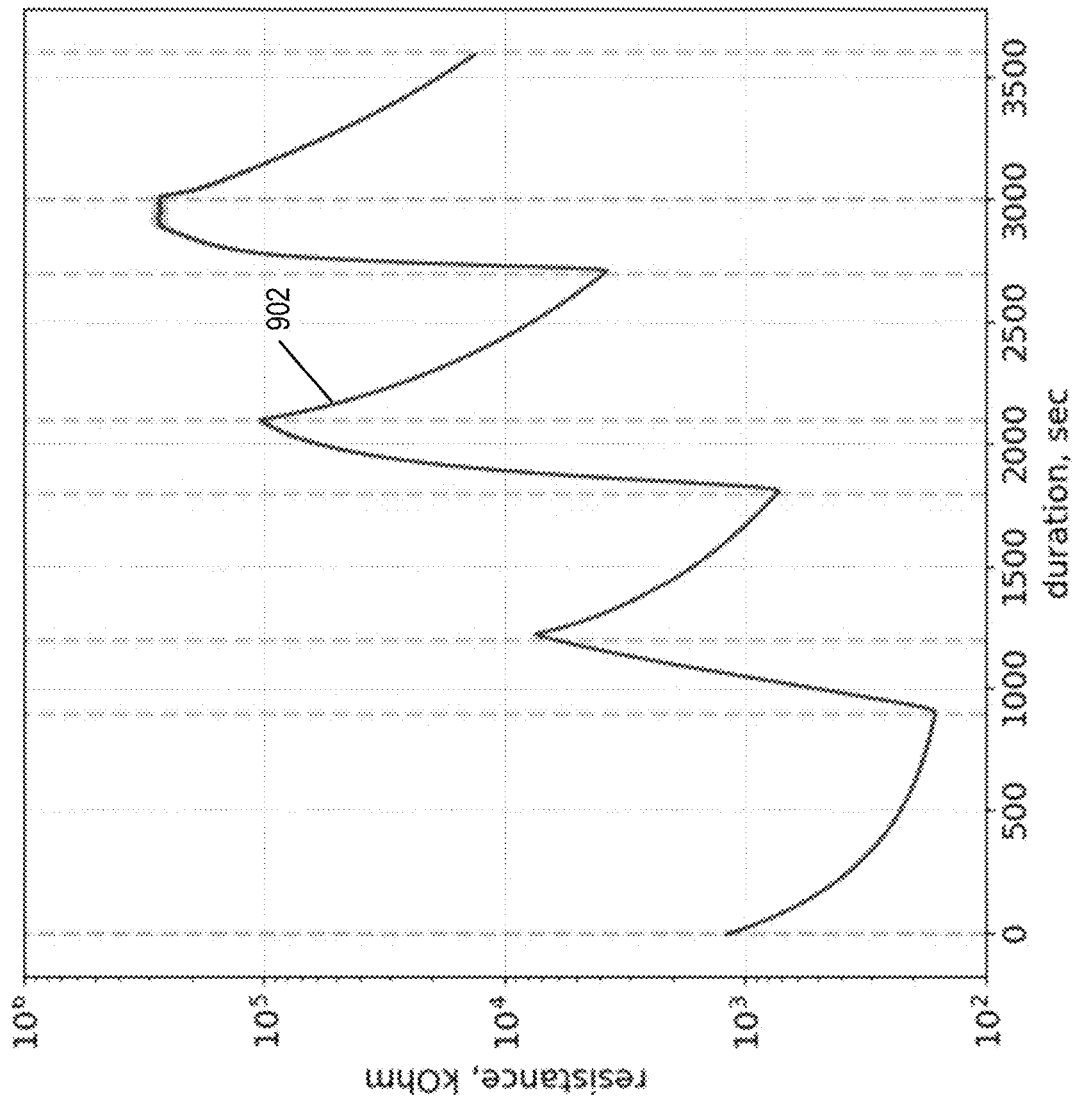
FIG. 9 shows 50-100-200 parts-per-billion (PPB) ozone at room temperature and 35% relative humidity (RH)

FIG. 9 shows a real-time sensing response 902 for 50-100-200 parts-per-billion (PPB) ozone (O3) exposure at room temperature and 35% relative humidity (RH). After an initial 15-minute air exposure, the sensor response resistance is plotted against time with on and off O3 exposure in 5- and 10-minute intervals, respectively. The resistance change divided by initial resistance ($\Delta R/R$) is >3500% at 50 ppb O3 exposure for this nanomaterial deposited onto an electrode.

Figure 10:
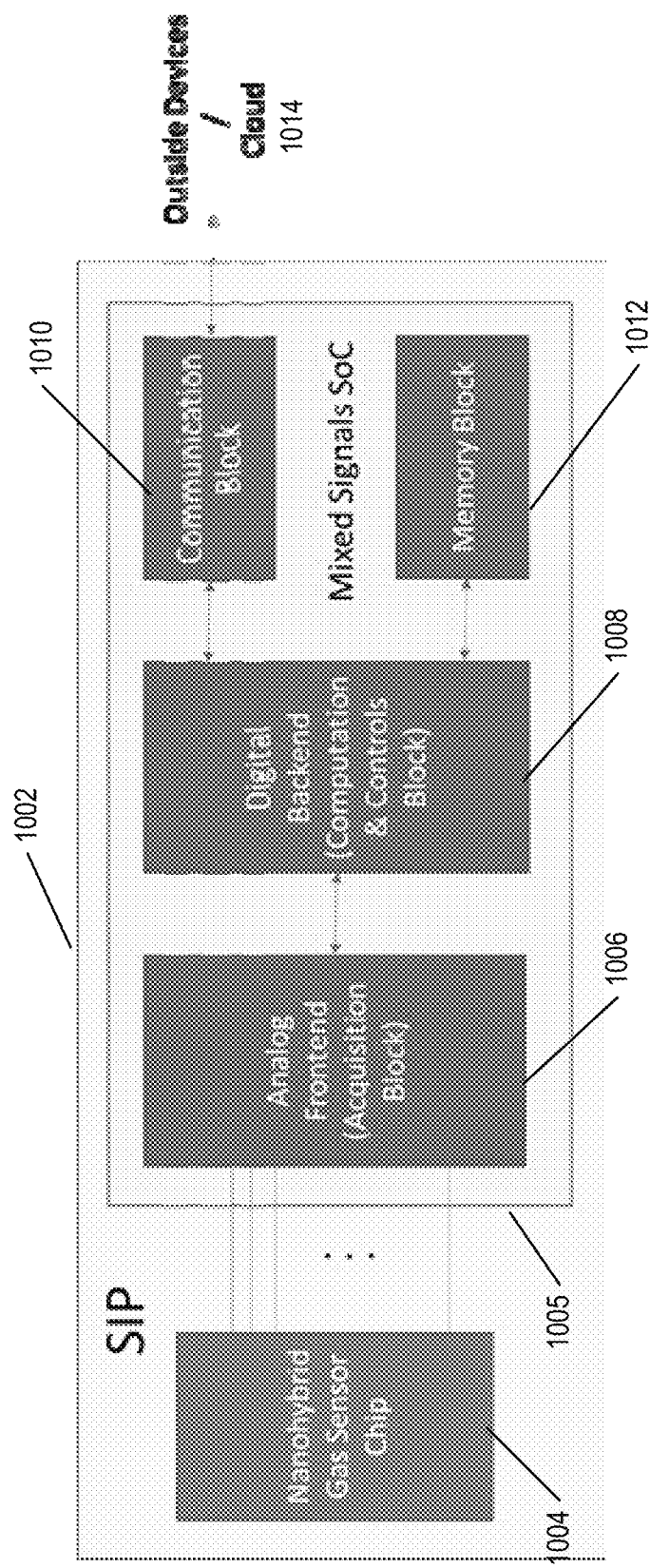
FIG. 10 shows a high-level block diagram of the complete SIP (System In a Package)

FIG. 10 shows a high-level block diagram of a complete nanohybrid gas sensor system 1002 in accordance with one example embodiment. System 1002 includes a sensor chip 1004 that can implement an array of nanohybrid gas sensing elements on a silicon substrate, such as the element illustrated in FIG. 8. A MEMS manufacturing process can be used to build the structure of the sensing channels on which nanomaterials specific to target gases will be deposited. The sensor chip 1004 can be connected to a mixed-signal SoC 105, which can be included within the same physical package, thus creating a SIP (System In a Package). The mixed-signals SoC 1005 implements a complete electronic subsystem specifically designed to interface to the sensor chip 1004, capture the analog signals from the sensing elements (as illustrated in FIG. 8), condition and convert them to digital format so pattern recognition algorithms running on a microcontroller integrated in the SoC 1005 can measure and predict gas concentration values, and make the results available to outside devices and applications 1014 running either locally or in the Cloud.

As can be seen, the signals from the sensing elements are fed to an analog front end 1006, which can be referred to as the signal acquisition block. The analog front end 1006 can acquire the signals from the sensing elements and condition them, as described below, before converting the signals to digital signals that can be sent to the Digital backend 1008. The digital backend 1008 can include a microcontroller, as noted to run algorithms on the signals to measure and predict gas concentration levels.

The SoC 1005 can also include memory 1012 to store data produced by the digital backend 1008 and possible to store instructions, e.g., for the microcontroller.

The SoC can also include a communication block, i.e., circuitry 1010 for communicating with external deices 1014. In certain embodiments, some or all of the circuits included in communications block 1010 can be included in the digital backend 1008.

Figure 11:
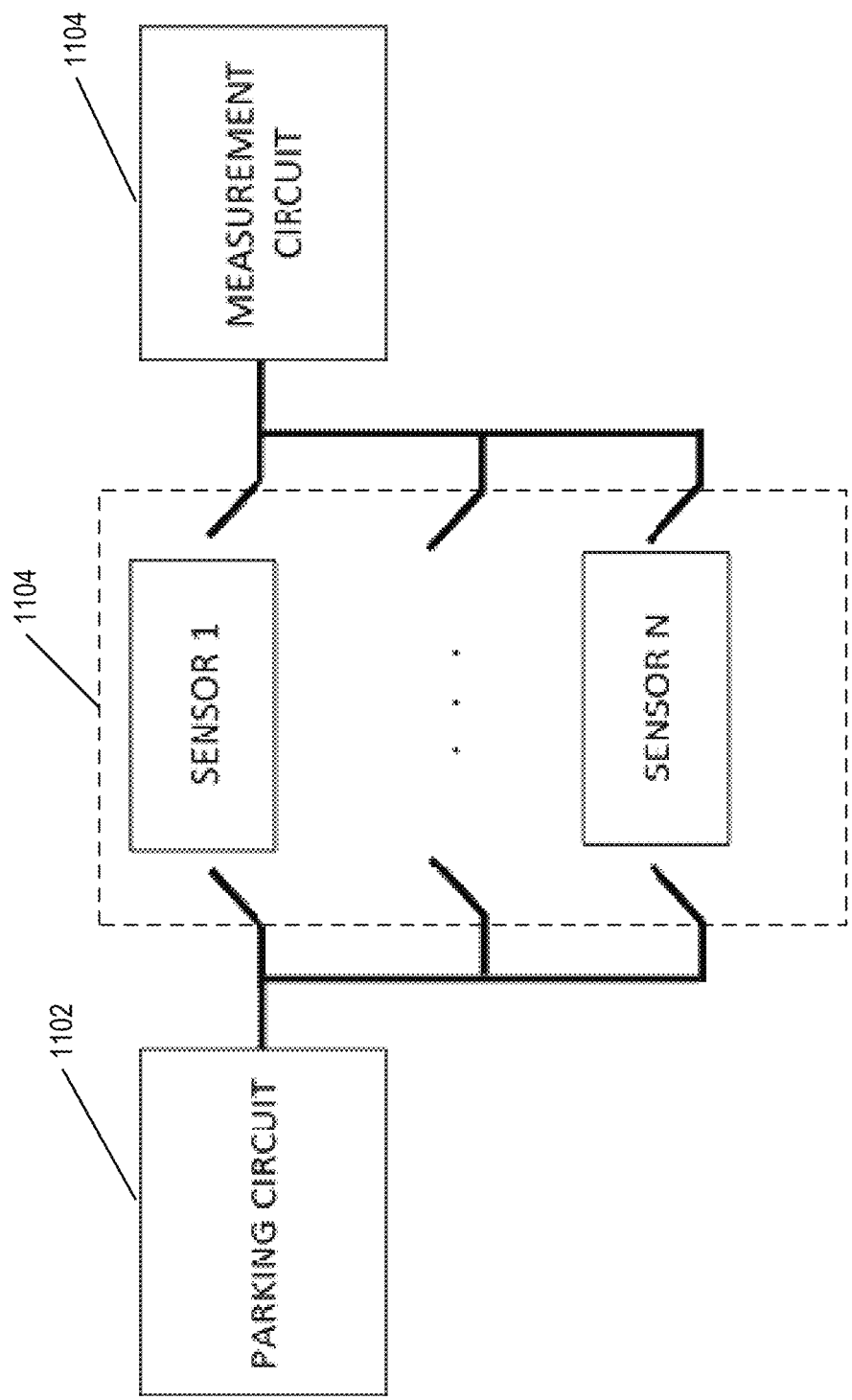
FIG. 11 shows simultaneous connection of multiple sensing channels to either parking or measurement circuits.

FIG. 11 shows a high-level representation of a key function implemented in the analog frontend portion of the SoC to allow the simultaneous connection of multiple sensing channels (1104) to either a parking 1102 or a measurement circuit 1106. The parking circuit 1102 is where the sensing channels 1104 are connected to when not being measured, i.e., connected to the measurement circuit 1106, and allows for conditioning of the sensing channels 1104 while waiting to be connected to the measurement circuit 1106. The parking circuit 1102 is designed to keep the sensing channels 1104 within the linear region of operation, and to effectively switch sensing channels between inactive and active (in measurement) modes while reducing the overall power consumption. The measurement circuit 1106 is designed to minimize settling times when switching channels.

Parking 1102 and measurement 1106 circuits allow for a make before break connection scheme to minimize transient loads on the sensing channels 1104.

Figure 12:
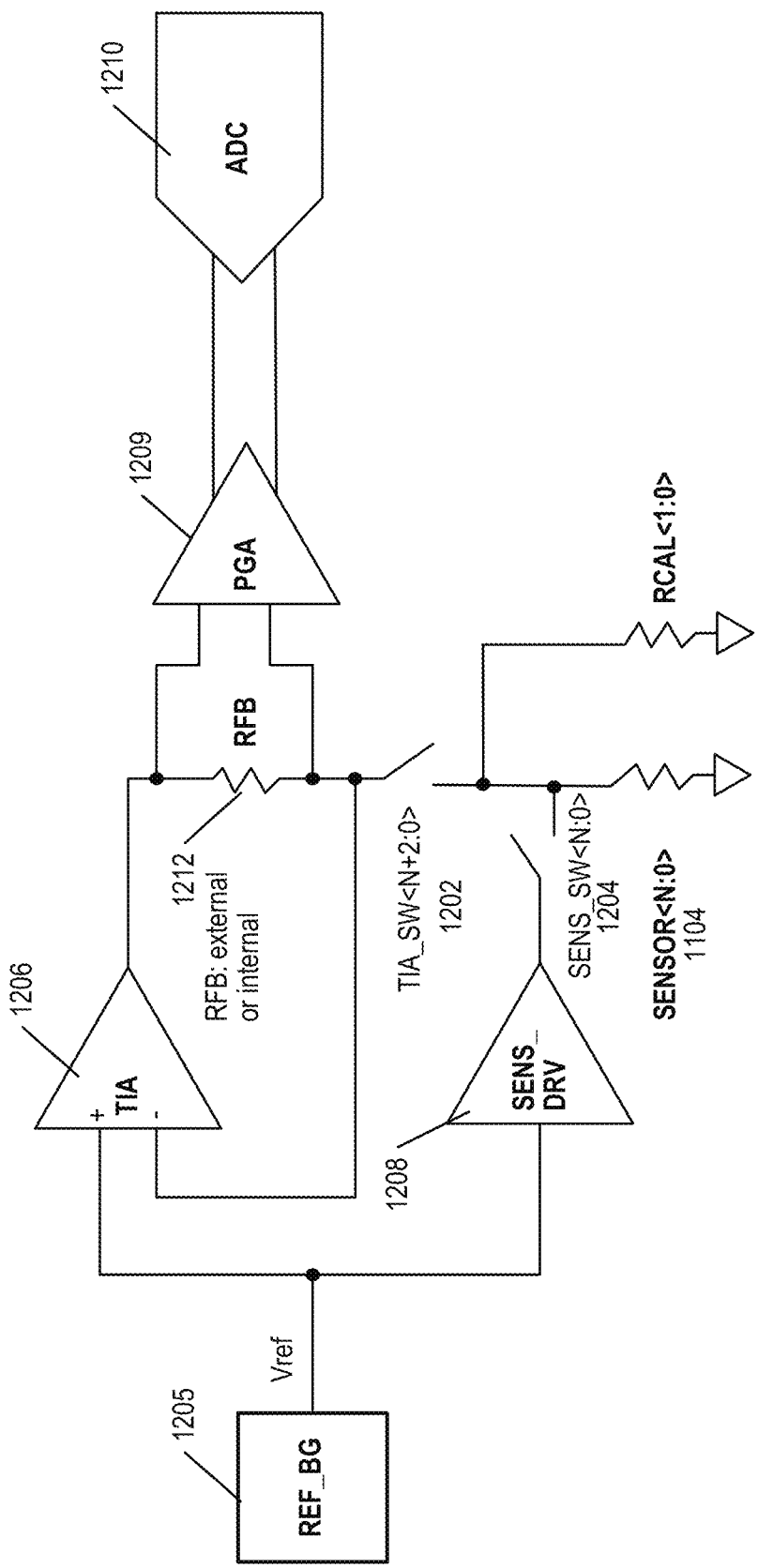
FIG. 12 shows a block diagram of a SoC implementation of the sensor drive and measure block.

FIG. 12 shows a block diagram of the SoC sensor data acquisition circuit 1200, which can be included parking circuit 1102 and measurement circuit 1106. It includes switch arrays 1202 and 1204 to select and drive up to N sensors, Sensor Driver (SENS_DRV) 1208, a transimpedance amplifier (TIA) 1206 and a programmable gain amplifier (PGA) 1208 to take sensor measurement, and an analog to digital converter (ADC) 1210 to convert each sensor measurement into a digital representation.

SENS_DRV 1208 consists of a low offset buffer capable of driving a continuous DC load current. It utilizes a reference voltage (Vref) output voltage from the reference block (REF_BG) 1206 to create a Vref buffered output that is used to force a Vref bias value across all parked sensors at all times. The value of Vref is selected to keep the sensors within the linear region of operation, reduce the overall power consumption, and provide a reasonable range of measurement for the digital logic.

The Sensor Driver 1208 includes an array of N low resistance switches 1204 to facilitate connection to the sensor array 1104. Each sensor can be connected to the driver buffer through a dedicated switch in the switch array 1204. The switch array 1204 is controlled by a N-bit control signal thereby giving the ability to control each switch state independently. This allows independent control of each sensor's park/measure state, including the ability to disconnect any number of unused or faulty sensors permanently, without affecting the operation of the remaining sensors. This arrangement can also allow random access of the sensor array 1104. Any number of sensors, up to the maximum of N, can be biased in the parked state in any combination.

The sensor resistance can be measured using TIA 1206. The TIA 1206 uses the calibrated Vref output voltage from the Reference block 1206, and a low offset buffer capable of driving a set minimum current of continuous dc load. The TIA 1206 forces a calibrated Vref dc across the Sensor To Be Measured (STBM) to measure the sensor resistance. The TIA 1206 transfer function is given by:

$$VOUT=(1+RFB/RS)VIN,$$

where RFB is the TIA feedback resistor 1212 and RS is the resistance of the STBM. The input voltage VIN is the calibrated Vref. The TIA 1206 generates a pair of differential output signals across the feedback resistor RFB. These signals are connected to the inputs of PGA 1208.

The design can include both external and internal options for the TIA feedback resistor 1212, which provides flexibility to adjust performance of the circuit. Similarly, the circuit can also include two external calibration resistors (RCAL<1:0>) 1214 that are intended to be used as a precision known resistor instead of a sensor element for calibrating both the unknown sensor, and the TIA feedback resistor 1212 in the event the internal resistor option is used.

The TIA 1206 includes an array of N low resistance switches 1202 to facilitate connection to the STBM. Each sensor can be connected to the TIA 1206 through a dedicated switch in the switch array 1202. The switch 1202 is controlled by a N-bit control signal thereby giving the ability to control each switch state independently. This allows for independent selection of the STBM in any order. The controller will allow both make before break and break before make switching of the STBM. Two additional switches are included to facilitate connection to the calibration resistors.

The sensor data acquisition circuit includes a differential PGA 1208 for adjustment of the gain. The PGA 1208 output signals are connected to the inputs of ADC 1210. The ADC 1208 can use a 16-bit second order Sigma Delta converter with 1-bit quantization to generate a digital representation of the PGA 1208 output voltage.

Figure 13:
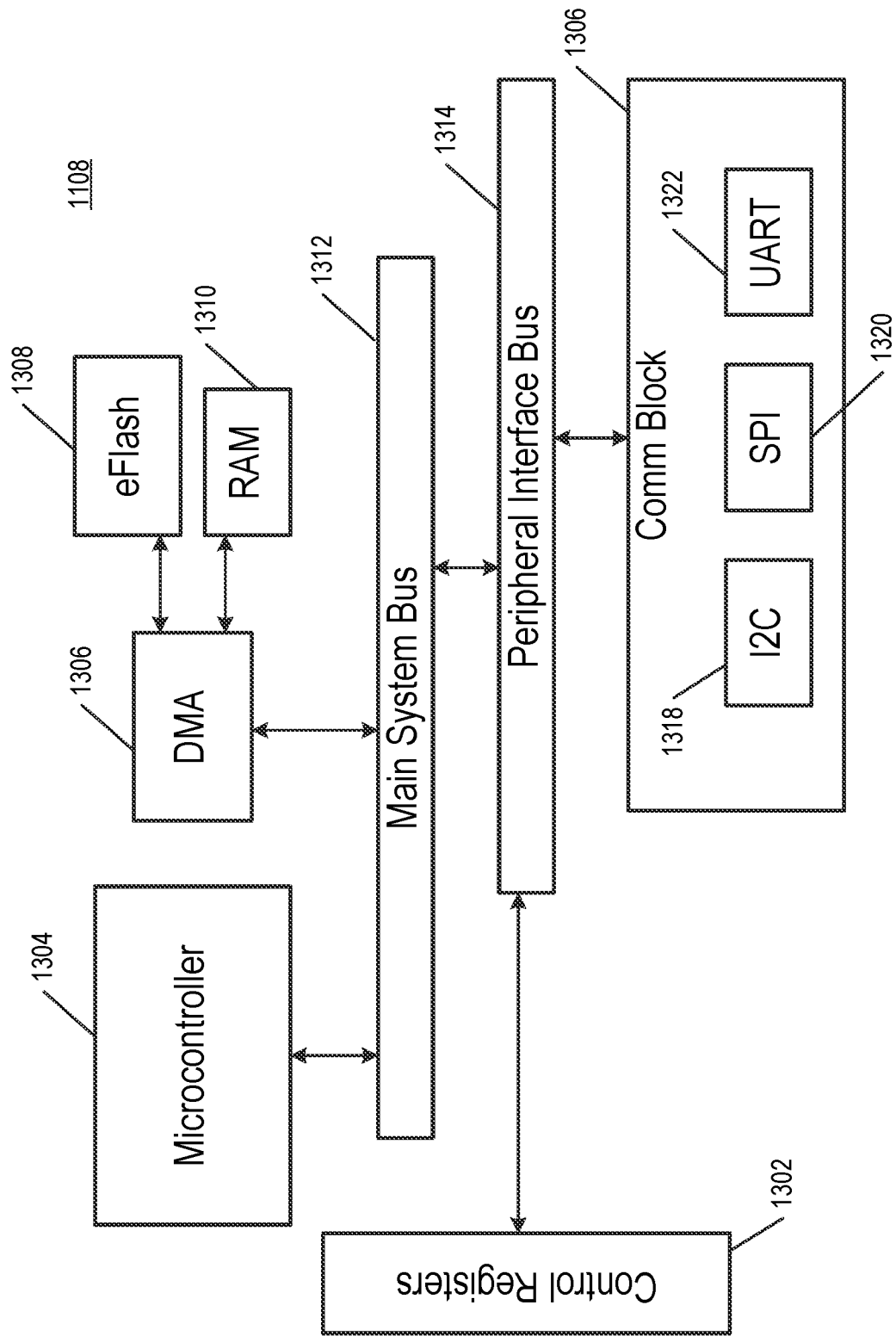
FIG. 13 shows a high-level block diagram of the SoC digital backend.

FIG. 13 shows a block diagram of the SoC digital backend 1008. Digital backend 1008 can be built around a very low power implementation of a microcontroller architecture optimized to deliver an optimum trade-off between computer speed, cost reduction, and power usage. An example instruction set architecture (ISA) that would satisfy these requirements is the open source RISC-V ISA.

In backend 1008, microcontroller 1304 provides controls to the analog frontend via a set of control registers 1302 to, among other things, optimize power delivery, sensor data collection, and gas concentration measurement. Microcontroller 1304 can be configured to predict gas concentration values by running specially optimized pattern recognition algorithms, developed to work specifically with the nanohybrid gas sensor chip 1004 and the SoC sensor data acquisition circuit 1200. The algorithm analyzes in real time the nanohybrid gas sensors multivariate output as it is acquired by the SoC's analog frontend and delivers very accurate concentration values for the target gases. The algorithm filters high frequency noise using an exponential average low pass filter and computes the transient response of the highly sensitive nano nucleated structures of the nanohybrid gas sensor array 1104 to changing gas concentration.

The microcontroller 1304 also manages the formatting and temporary storage of the gas information together with other related metadata that may be collected for a specific application. In the preferred embodiment, gas information data storage is done in an embedded flash memory (eFlash) 1308.

Finally, the microcontroller 1304 uses a communication block 1316 to control the exchange of data in and out of the system. In a preferred embodiment targeting an IoT application, the communication block 1316 can provide several serial communication interfaces such as the I2C 1318, UART 1322, and SPI 1320 interfaces as shown; however, different applications in different industries may require other interfaces, either ready available as IP block from a variety of vendors (such as USB) or possibly custom-designed to a customer's specifications. For wearable device applications, the communication block 1316 can include a wireless interface such as Bluetooth Low Energy (BLE) to communicate with a device such as a cell phone running a mobile application to visualize the sensor data and possibly to upload it to a Cloud data platform.

The digital backend can also comprise various buses, e.g., buses 1312 and 1314 to all communication between the various blocks.

Figure 14:
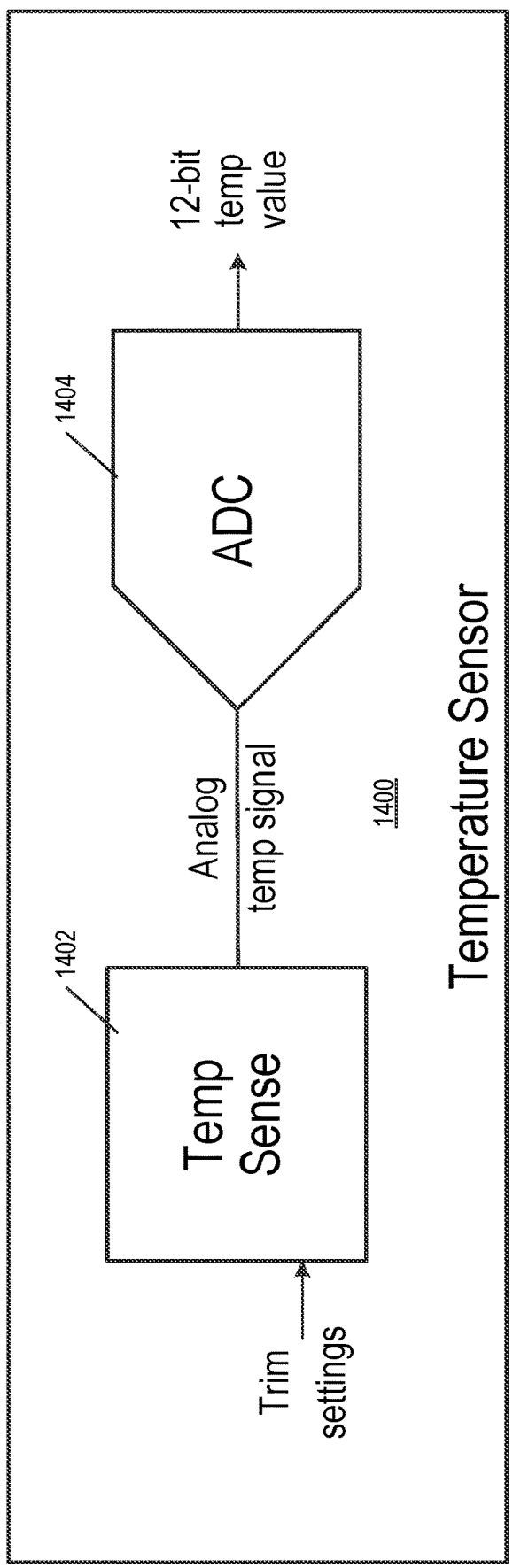
FIG. 14 shows a block diagram of the integrated temperature sensor circuit.

FIG. 14 is the block diagram of an integrated temperature sensor 1400 that can be integrated into the system 1002. The sensor system 1002 needs to take temperature and humidity (both local to the sensor array) into consideration when measuring the sensors' response to changes in gas concentration. Humidity, which is a gas, can be measured by appropriately functionalizing a subset 1402 of the sensor array 1104 itself. Temperature can be measured by implementing a dedicated temperature sensor on the SoC 1005, which can then sense the operating temperature of the gas sensor array when the MEMS sensor chip 1004 is, e.g., stacked on top of the SoC 1005 in a SIP configuration. In the preferred embodiment, the temperature sensor is constructed with internal bipolar transistors; a differential implementation with two complementary bipolar devices is used to develop a large temperature signal. A dynamic element matching technique can be used to minimize mismatch errors. The temperature sensor 1400 can use a first order Sigma Delta ADC 1404 to deliver a 12-bit temperature output. In the preferred embodiment, the temperature sensor can detect temperatures in the range from −40 C to 85 C with an accuracy of ±1 C. Multiple trim settings can be implemented to adjust the performance of the temperature sensor (e.g. reference voltage gain trim); trim parameters can be stored in an embedded Flash memory 1308.

Figure 15:
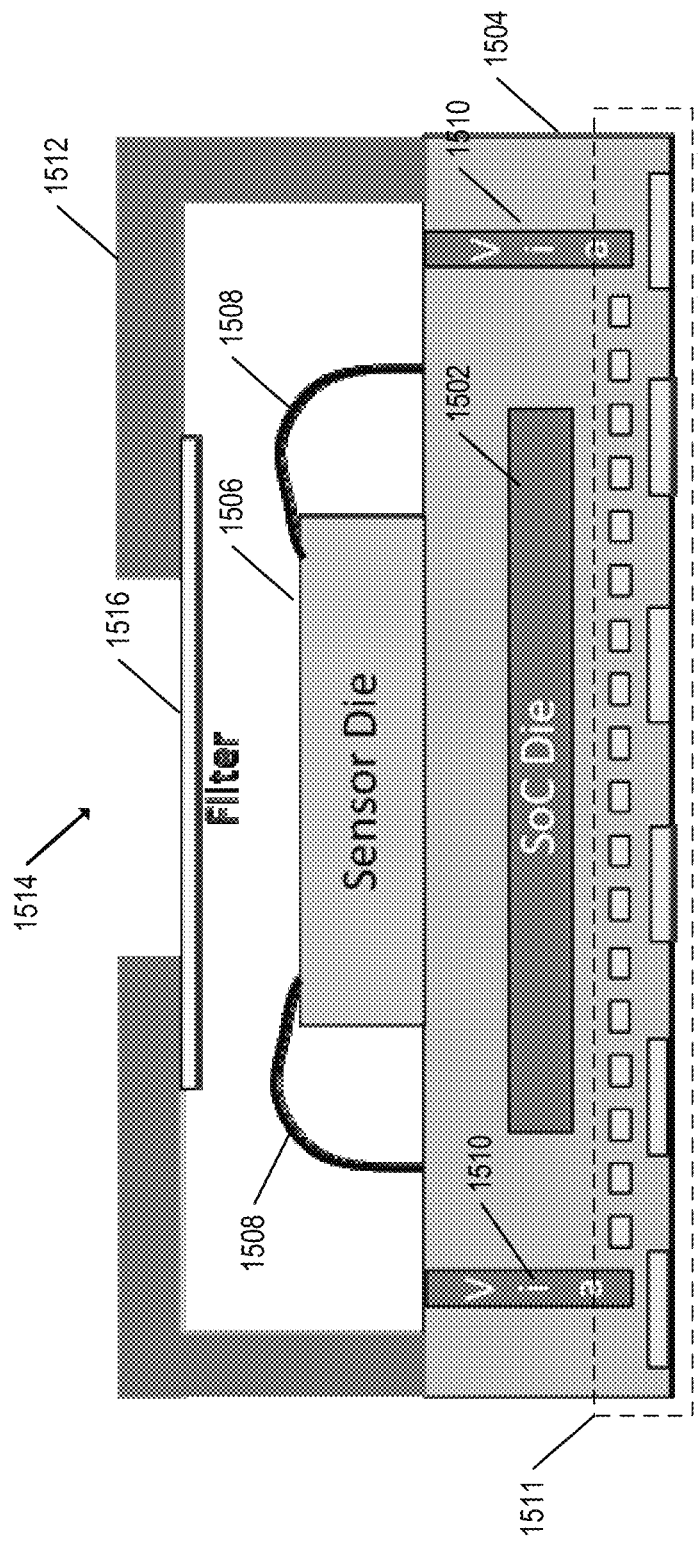
FIG. 15 shows a System In a Package (SIP) conceptual diagram.

FIG. 15 shows a conceptual view of an example SIP configuration for system 1002. The SoC die 1502 is embedded in the thickness of the package substrate 1504, the sensor chip 1506 is wire-bonded by wires 1508 to traces (not shown) in the package that connect through vias 1510 to the related SoC pads 1511. The package illustrated in FIG. 15 is a LGA (Land Grid Array). The package can include a lid 1512 that includes a hole 1514 to provide an air interface to the sensor chip 1506. A filter 1516 is included in order to provide dust and moisture protection to the sensor chip 1506. The X-Y dimensions of the package are modulated by SoC die area and package technology Design For Manufacturability (DFM) rules. The Z dimension is modulated by thickness of the stacked components (substrate 1504, SoC die 1502, sensor die 1506, filter).

While nanohybrid gas sensors do not require heating in order to function, it can be useful in some applications to have the ability to heat the sensor chip 1506. Thus, in certain embodiments, the SoC 1002 includes distributed heating elements placed between the pads 1511 in the pad ring. This is arranged into an array with each heating element comprising a resistor in series with an NMOS switch connected between VDD and VSS power rails. The switch is controlled by a pulse width modulated signal from the microcontroller 1304. The heater array can be used to intermittently raise the temperature of the sensor chip 1506. A temperature sensor 1400 can then be used to monitor the approximate resulting temperature.

Figure 7:
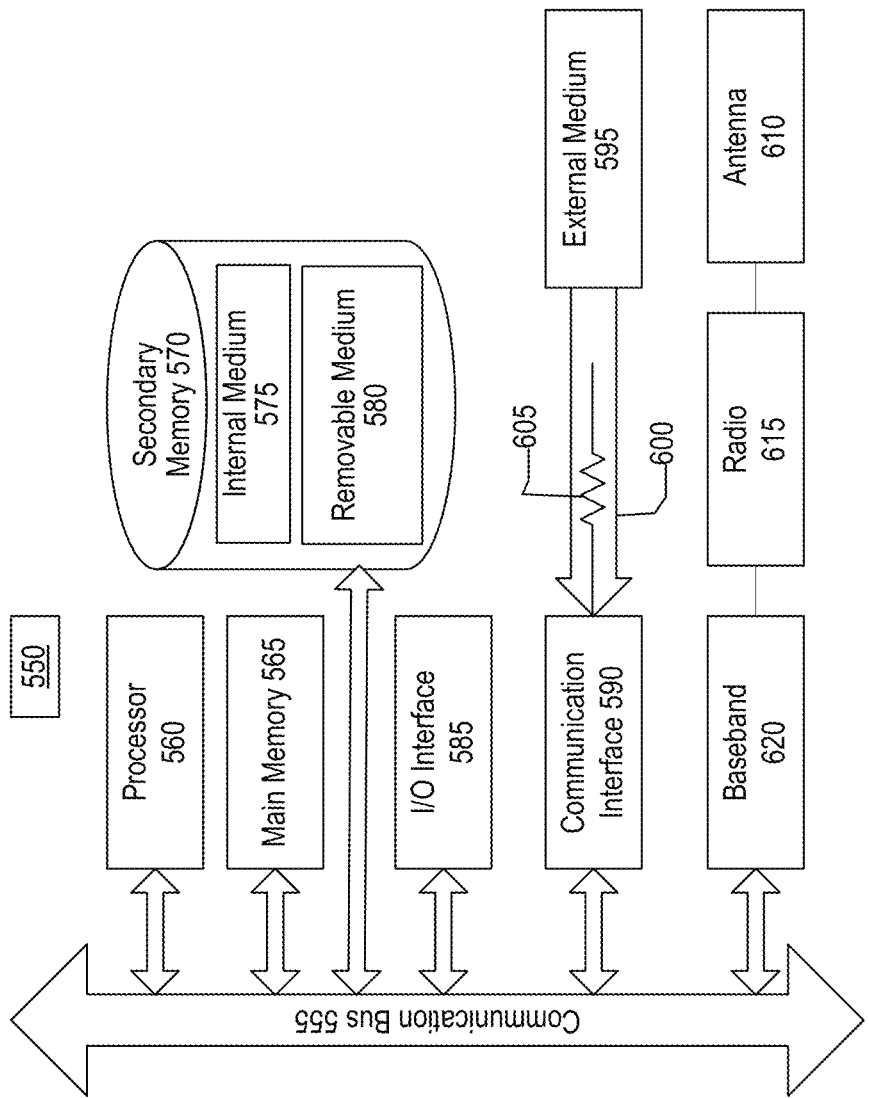
FIG. 7 is a block diagram illustrating an example wired or wireless system that can be used in connection with various embodiments described herein.

FIG. 7 is a block diagram illustrating an example wired or wireless system 550 that can be used in connection with various embodiments described herein. For example the system 550 can be used as or in conjunction with one or more of the platforms, devices or processes described above, and may represent components of a device, such as sensor 400, the corresponding backend or cloud server(s), and/or other devices described herein. The system 550 can be a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif. Example processor that can be used in system 400 include the ARM family of processors and the new open source RISC-V processor architecture.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Pearl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed is:

1. A sensor system in a package, comprising:
a package, the package including:
a sensor chip comprising a sensor array comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when interacting with gaseous chemical compounds; and
a mixed signal System on a Chip (SoC), comprising:
an analog signal conditioning and Analog-to-Digital conversion circuit configured to convert an analog signal into a digital signal, wherein the analog signal conditioning and Analog-to-Digital conversion circuit further comprises a parking circuit and a measurement circuit, wherein the plurality of sensing elements are connected to the parking circuit when not connected to the measurement circuit, and wherein the parking circuit is further configured to keep the plurality of sensing elements within a linear region of operation, and to effectively switch the plurality of sensing elements between inactive and active modes while reducing the overall power consumption, and
a low-power processor circuit configured to process the digital signal using a pattern recognition system implementing gas detection and measurement algorithms.

2. The sensor system in a package of claim 1, wherein the mixed signal SoC further comprises a memory, coupled with the low-power processor circuit, the memory configured to store algorithms combining models that accurately reflect a behavior of sensing elements customized with the specific molecular formulation, and instruction that cause the processor to perform pattern recognition techniques to convert a raw sensor output into gas concentration readings based on the algorithms and models.

3. The sensor system in a package of claim 1, wherein each of the plurality of sensing element is designed such that the hybrid nanostructures and molecular formulations can be deposited using drop casting or electro-chemical deposition.

4. The sensor system in a package of claim 1, wherein each of the plurality of sensing element comprises a MEMS substrate.

5. The sensor system in a package of claim 1, wherein the measurement circuit is configured to minimize settling times when the plurality of sensing elements are being switched between the parking circuit and the measurement circuit.

6. The sensor system in a package of claim 1, wherein the parking and measurement circuits allow for a make before break connection scheme to minimize transient loads on the plurality of sensing elements.

7. The sensor system in a package of claim 1, wherein the parking and measuring circuits comprise switch arrays configured to select and drive up to N sensor elements, which comprise the plurality of sensor elements, a sensor driver, a reference block, a transimpedance amplifier (TIA), a programmable gain amplifier (PGA) configured to take sensor measurement, and an analog to digital converter (ADC) configured to convert each sensor measurement into a digital representation.

8. The sensor system in a package of claim 7, wherein the sensor driver comprises a low offset buffer capable of driving a continuous dc load current and configured to use a reference voltage (Vref) output voltage from the reference block to create a Vref buffered output that is used to force a Vref bias value across all sensor elements of the plurality of sensor elements that are connected to the parking circuit.

9. The sensor system in a package of claim 8, wherein the value of Vref is selected to keep the plurality of sensor elements that are connected with the parking circuit within a linear region of operation, reduce the overall power consumption, and provide a reasonable range of measurement for the low-power processor circuit.

10. The sensor system in a package of claim 8, wherein the sensor driver includes a switch array of N low resistance switches to facilitate connection to the plurality of sensor elements such that each of the plurality of sensor elements can be connected to a low offset buffer through a dedicated switch in the switch array.

11. The sensor system in a package of claim 7, wherein the TIA is configured to measure the resistance of a sensor element in the plurality of sensor elements using a calibrated Vref output voltage from the Reference block, and a low offset buffer capable of driving a set minimum current of continuous dc load by forcing a calibrated Vref dc across the sensor element to be measured to measure the sensor resistance.

12. The sensor system in a package of claim 11, wherein the TIA transfer function is given by: VOUT=(1+RFB/RS) VIN, where RFB is the resistance of a TIA feedback resistor and RS is the resistance of the sensor element to be measured, and VIN is the calibrated Vref.

13. The sensor system of claim 12, wherein the TIA generates a pair of differential output signals across the feedback resistor, and wherein the differential output signals are provided to the PGA.

14. The sensor system in a package of claim 12, wherein the feedback resistor can be an external resistor, an internal resistor, or both.

15. The sensor system in a package of claim 14, further comprising two external calibration resistors configured to provide a precision known resistor instead of a sensor element for calibrating both an unknown sensor element and the feedback resistor in the event the internal resistor is used for the feedback resistor.

16. The sensor system in a package of claim 15, wherein the TIA includes an array of N low resistance switches to facilitate connection to sensor elements of the plurality of sensor elements.

17. The sensor system in a package of claim 16, further comprising additional switches are included to facilitate connection to the calibration resistors.

18. The sensor system in a package of claim 7, wherein the PGA output signals are connected to the inputs of the ADC, and wherein the ADC uses a 16-bit second order Sigma Delta converter with 1-bit quantization to generate a digital representation of the PGA output voltage.

19. The sensor system in a package of claim 1, wherein a subset of the plurality of sensor elements are configured to measure humidity.

20. The sensor system in a package of claim 1, wherein the SoC further comprises a dedicated temperature sensor that can then sense an operating temperature of the gas sensor array.

21. The sensor in a package of claim 20, wherein the temperature sensor comprises internal bipolar transistors in a differential configuration.

22. The sensor in a package of claim 1, wherein the sensor chip is stacked on top of the SoC within the package, and wherein the package is a Land Grid Array.

23. The sensor in a package of claim 22, wherein the package comprises a lid, and the lid comprises a hole that provide an air interface to the sensor chip.

\* \* \* \* \*